United States Patent [19]

Hammond

[11] Patent Number: 4,626,184
[45] Date of Patent: Dec. 2, 1986

[54] SCARFING APPARATUS

[75] Inventor: Philip G. Hammond, Appleton, Wis.

[73] Assignee: Kimberly-Clark Corporation, Neenah, Wis.

[21] Appl. No.: 711,789

[22] Filed: Mar. 14, 1985

[51] Int. Cl.⁴ .................. B29D 7/00; A61F 13/16
[52] U.S. Cl. .................... 425/83.1; 264/167; 83/874
[58] Field of Search ...... 425/83.1; 264/167, DIG. 75; 83/874

[56] References Cited

U.S. PATENT DOCUMENTS

| | | | |
|---|---|---|---|
| 2,336,744 | 12/1943 | Manning | 264/DIG. 75 |
| 2,902,091 | 9/1959 | Dahle | 83/176 |
| 2,919,742 | 1/1960 | Schubert et al. | 425/83.1 |
| 3,230,287 | 1/1966 | Caron et al. | 425/83.1 |
| 3,470,286 | 9/1969 | Weber | 264/167 |
| 3,574,809 | 4/1971 | Fairbanks et al. | 264/167 |
| 3,730,031 | 5/1973 | Huttemann | 83/874 |
| 3,975,222 | 8/1976 | Mesek | 156/276 |
| 4,167,378 | 9/1979 | Hagg et al. | 425/82.1 |

Primary Examiner—Tim Miles
Attorney, Agent, or Firm—John L. Chiatalas

[57] ABSTRACT

A scarfing method and apparatus are disclosed for making a longitudinally and transversely contoured batt on a moving fibrous web. The apparatus comprises a scarfing roll disposed on one side of a foraminous belt and a contouring roll, having a nonuniform surface, disposed on the opposite side of the belt. As the contouring roll is rotated, it raises the belt and the fibrous web towards the scarfing roll, according to the shape of the nonuniform surface. Hence, a contour is provided in the direction of movement of the web. The transverse contour can be provided by the shape of the scarfing roll itself.

7 Claims, 4 Drawing Figures

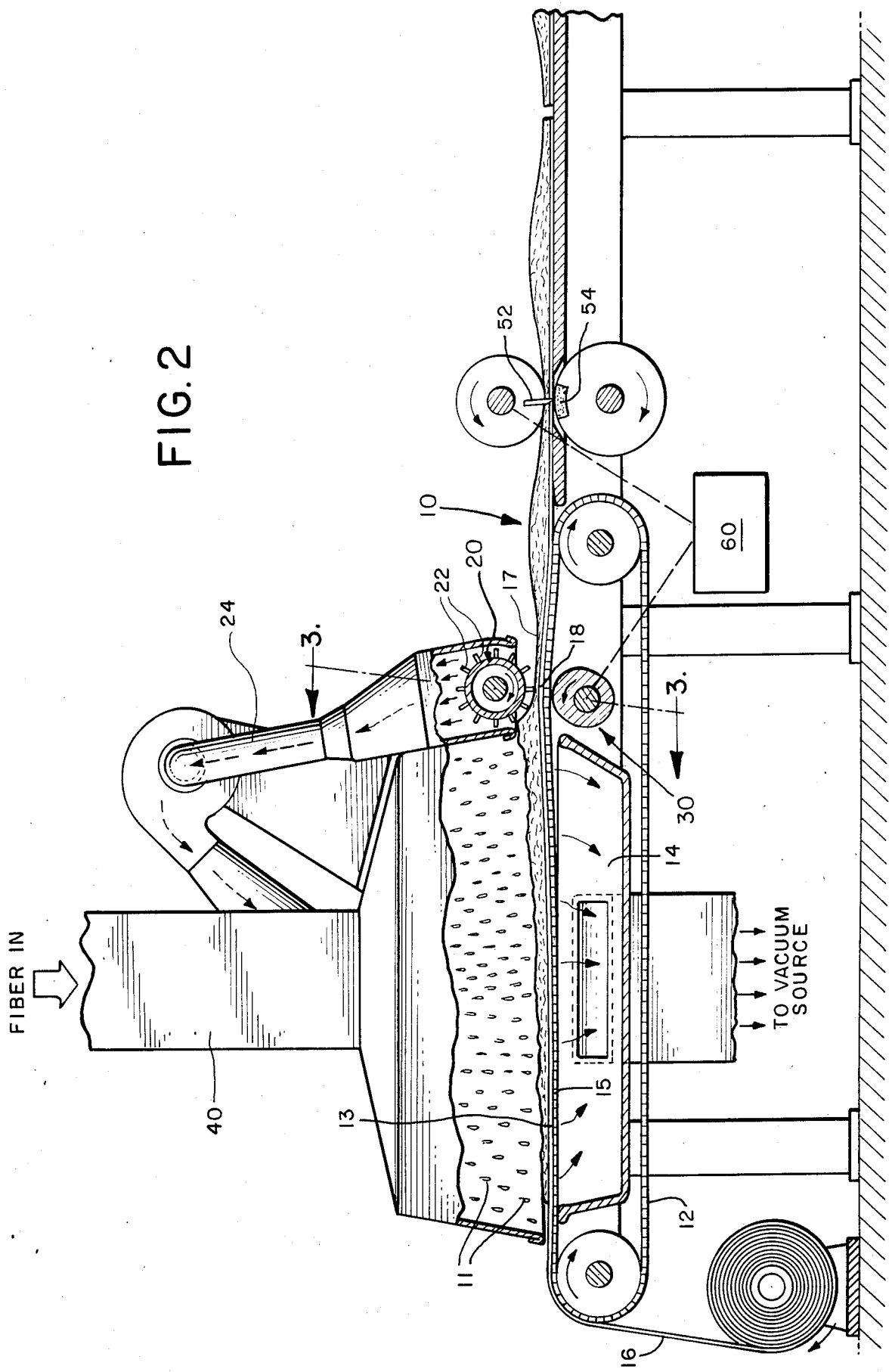

SCARFING APPARATUS

BACKGROUND OF THE INVENTION

This invention relates generally to absorbent structures including an impervious backing sheet, a liquid-permeable facing sheet and a batt disposed therebetween. More specifically, the invention relates to a contoured batt, and a method and apparatus for contouring the batt.

Batts for absorbent structures are often manufactured by air-forming a fibrous web on a continuous moving foraminous wire or screen. A fluff forming chamber deposits fibers onto a first surface of the screen or onto a pervious web, such as tissue, carried on this surface of the screen. A vacuum box beneath an opposing surface of the screen creates a pressure drop between the forming chamber and the screen, thereby facilitating the accumulation of fibers on the screen. A scarfing roll can be positioned downstream from the forming chamber to rake or scarf the fibrous web such that a substantially uniform surface is obtained by removing excess or unwanted fibers.

In some applications, it is desirable that batts formed in this manner be contoured such that they are thicker in some portions than in others. For example, it might be desirable to form the batts such that they are thicker in their central portions than in their marginal portions.

One method of forming contoured batts is disclosed in U.S. Pat. No. 3,975,222 to Mesek. According to this method, a transverse contour is provided by superimposing a narrower strip of compacted fibers upon a wider strip, and a longitudinal contour is provided by varying the rate of feed of the strips. However, this method is not without drawbacks, for example because the use of two sources of fibers and the variation of the feed rate can diminish the efficiency of the process.

SUMMARY OF THE INVENTION

This invention is directed to an improved scarfing method, apparatus and product made therefrom.

According to a first aspect of the invention, an improvement is provided to the batt portion of an absorbent structure. The absorbent structure includes an impervious backing sheet, a liquid-permeable facing sheet and a batt disposed between the backing and facing sheets. The improvement to the batt comprises an integrally formed, longitudinally and transversely contoured scarfed surface.

According to a second aspect of the invention, a method is provided for making a batt from a moving fibrous web having opposing surfaces. According to this method, a scarfing roll is provided for scarfing the web. The scarfing roll is positioned adjacent to a first surface of the web and rotated to form a transverse contour in the web by scarfing the first surface of the web. A contouring roll is provided, having a nonuniform circumferential surface disposed about a longitudinal axis. The contouring roll is positioned in communication with an opposing surface of the web, such that at least one portion of the circumferential surface of the scarfing roll will move the opposing surface of the web with respect to the axis of the scarfing roll if the scarfing roll is fully rotated about that axis. The contouring roll is rotated, such that each batt formed is contoured in the direction of movement of the web.

According to a third aspect of the invention, an improved apparatus is provided for making a batt from a moving fibrous web. The apparatus comprising a fibrous web carried on a moving belt, and a scarfing roll positioned above the web. The improvement comprises a contouring roll, having a nonuniform surface disposed about a longitudinal axis, positioned in communication with the belt.

An important object of this invention is to provide a method for longitudinally and transversely contouring a batt without the necessity of varying the speed of the belt carrying the fibrous web.

Another object of the invention is to provide a method for longitudinally and transversely contouring the batt without the requirement of varying the fiber feed rate into the forming chamber.

Still a further object of the invention is to provide a scarfing system that offers more precise bulk control than a system wherein the fiber feed rate is varied.

Further objects and attendant advantages of the invention will be best understood upon reading the following detailed description in connection with the drawings.

BRIEF DESCRIPTION OF THE DRAWINGS

FIG. 2 is a partial longitudinal cross-sectional view taken along line 2—2 of FIG. 1.

DETAILED DESCRIPTION OF THE PREFERRED EMBODIMENTS

Figure 1:
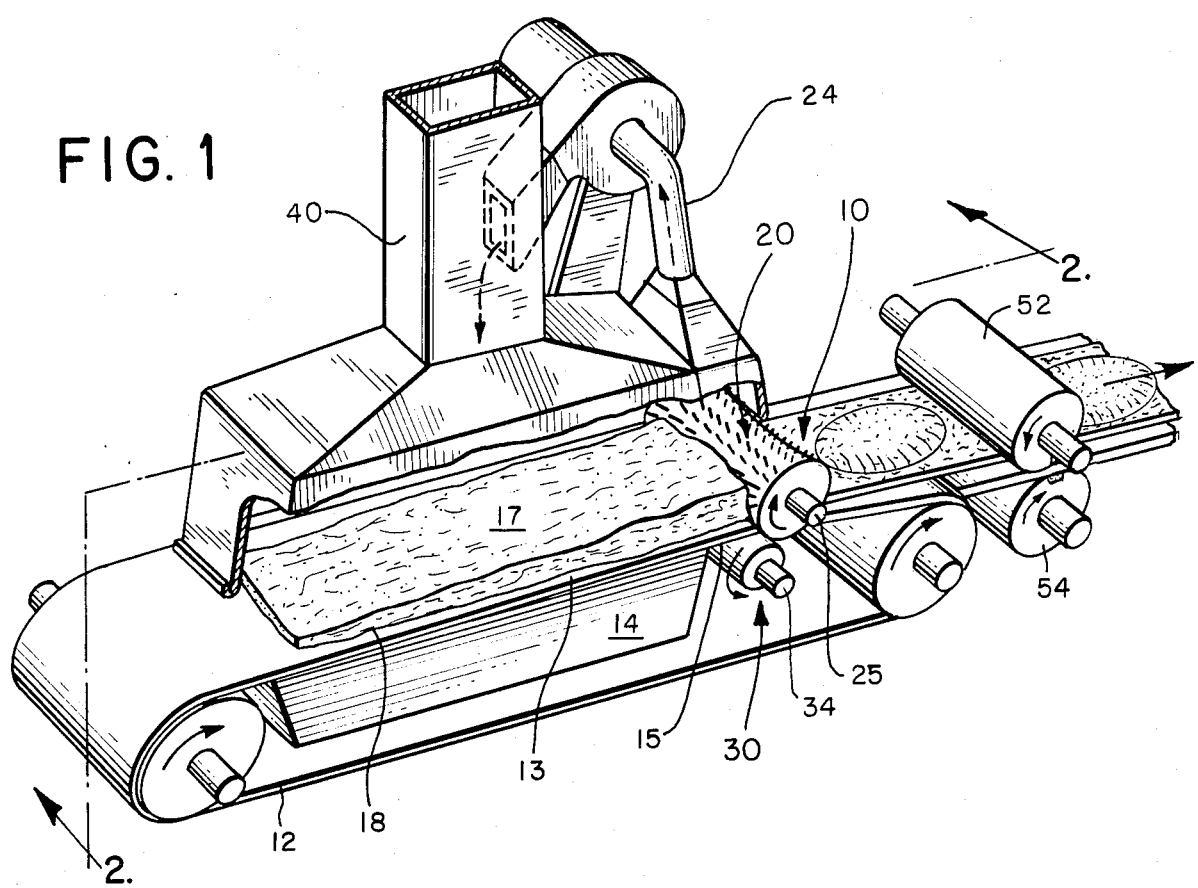
FIG. 1 is a perspective view of the formation of a batt for a preferred embodiment of the present invention.

Turning now to the drawings, FIG. 1 shows a moving fibrous web 10 being scarfed by a scarfing roll 20 and being contoured by a contouring roll 30. The fibrous web 10 is disposed upon a foraminous belt 12 which is in turn disposed over a vacuum box 14. The web 10 is formed by the dispensation of cellulosic fibers from a fluff forming chamber 40. If desired, a tissue liner 16 can be provided under the fibrous web 10 between the web 10 and the belt 12 as shown in FIG. 2.

The fibrous web 10 is formed by randomly distributing loose fiber 11, conveyed by air, onto the belt 12 or the tissue liner 16. The tissue liner may be a simple water pervious tissue wrap containing the batt or may be a more sophisticated liner material of a type known in the art for use as a body side water pervious liner or facing sheet; in use, as aforementioned, the absorbent structure would integrate the fibrous batt between such a water-pervious facing sheet and an impervious backing sheet, e.g. polyethylene film. A first or upper side 13 of the belt 12 or tissue liner 16 receives the fiber, while an opposing second or lower side 15 of the belt 12 is abutted in the forming area by the vacuum box 14, which causes a pressure drop in the air across the belt 12 and facilitates accumulation of fiber onto the moving fibrous web 10.

The scarfing roll 20 rotates against the moving fibrous web 10 at an upper or first surface 17 of the web 10. For the purposes of this disclosure, the terms "upper" and "lower" are used for convenience, but are meant to be taken generically in the sense of a "first" and "second" side respectively. The scarfing roll 20 is provided with a plurality of scarfing teeth 22 for scarfing the upper surface 17 of the web 10. In the preferred embodiment, the teeth 22 are arranged to form an arched scarfing surface 26.

The contouring roll 30 is disposed on the lower side 15 of the belt 12, preferably directly adjacent to the vacuum box 14. The contouring roll 30 comprises a nonuniform circumferential surface 32 disposed about a longitudinal axis 34. In the preferred embodiment, the nonuniform circumferential surface includes a bowed surface 36 and a flattened surface 38, The contouring roll 30 rotates about the longitudinal axis 34 such that during at least a part of the rotation, the circumferential surface 32 abuts the lower side 15 of the belt 12, causing it to move in a direction away from the longitudinal axis 34. Thus, a lower surface 18 (opposite the upper surface 17) of the moving fibrous web 10 is brought into closer proximity with the plurality of scarfing teeth 22 of the scarfing roll 20. In this manner, a longitudinal contour is provided in the moving fibrous web 10.

Figure 3:
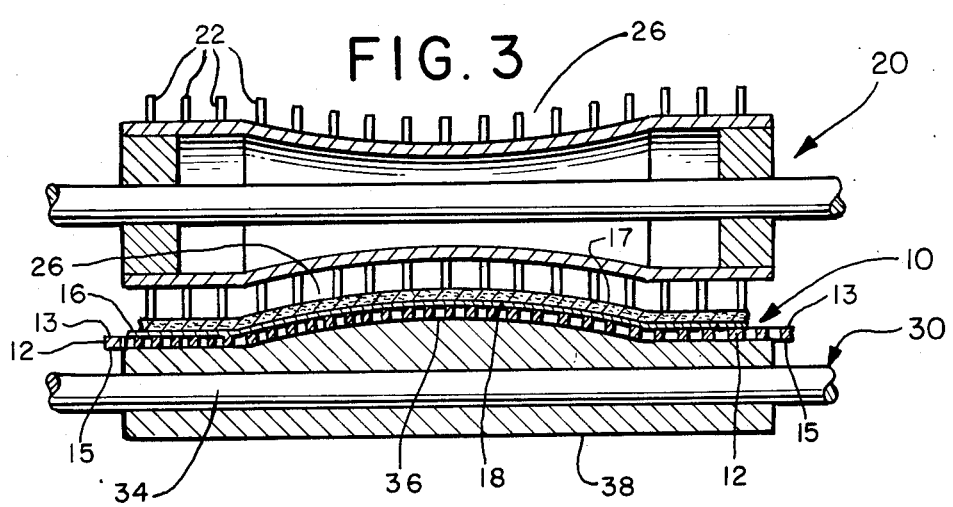
FIG. 3 is a transverse cross-sectional view taken along line 3—3 of FIG. 2.
Figure 4:
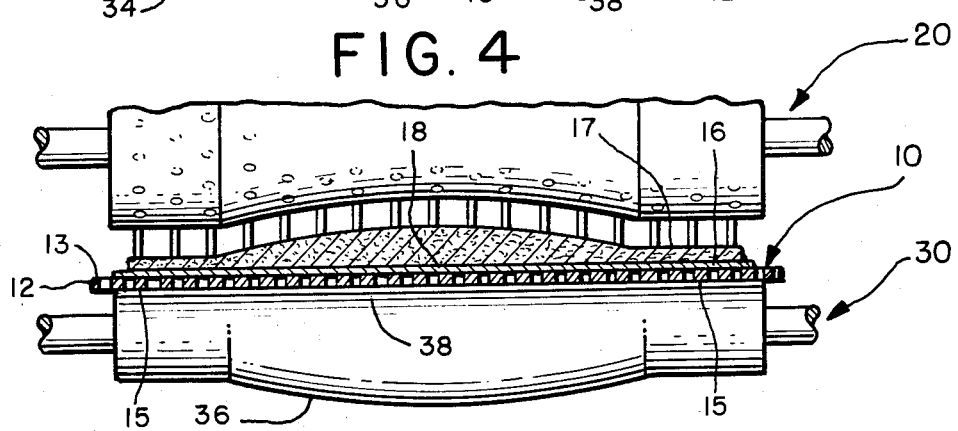
FIG. 4 is a transverse cross-sectional view similar to that of FIG. 3, but with the contouring roll rotated about its axis.

FIGS. 3 and 4 show the contouring roll 30 in different positions of rotation about its longitudinal axis 34. In FIG. 3, the bowed surface 36 of the contouring roll 30 is abutting the lower side 15 of the belt 12, thereby causing the moving fibrous web 10 to rise in the region of the scarfing roll such that the longitudinal contour is decreased. In contrast, in FIG. 4 the contouring roll 30 is exposing the flatened surface 38 against the lower side 15 of the belt 12. Accordingly, the upper surface 17 of the moving fibrous web 10, scarfed by the scarfing roll 20, is disposed at a greater distance from the lower surface 18 of the fibrous web 10, such that a thicker longitudinal contour is formed. As can be ascertained from the Figures, it is presently preferred that the resultant batt be contoured such that it is thickest in its central portions relative to its marginal portions.

Two other aspects of the preferred embodiment are best seen in FIG. 2. Specifically, the scarfing roll 20 sends the excess fluff fibers through a recycling chute 24 which in turn passes the fluff back to the forming chamber 40. Additionally, a knife 52 and anvil 54 are placed downstream the scarfing roll 20 and contouring roll 30 respectively, to separate the batts formed by the scarfing/contouring operation.

It is preferred that the contouring roll 30 be timed to rotate once per batt formed, although in certain applications it will be appropriate to provide a repeating pattern on the nonuniform circumferential surface 32 and form a plurality of batts in a single revolution of the roll 30. Accordingly, the rotation of the contouring roll 30 and the knife 52 is preferably synchronized by a conventional timing mechanism 60.

The following parameters for the apparatus and method of the present invention are given by way of illustration, and not limitation, to show the possibilities contemplated by the inventor for the operation of the present invention.

The scarfing roll 20 is preferably a contoured roll in which the scarfing teeth 22 define the arched scarfing surface 26. At its largest transverse cross-sectional area, the scarfing roll has a diameter preferably in the range of from about 5 inches to about 7 inches, and at its smallest transverse cross-sectional area, the scarfing roll has a diameter preferably in the range of from about $3\frac{1}{2}$ inches to about $5\frac{1}{2}$ inches. It is presently most preferred that the arched scarfing surface 26 will be sized and contoured such that its greatest transverse cross-sectional radius will be about $3\frac{1}{2}$ inches, and its least transverse cross-sectional radius will be about $2\frac{1}{2}$ inches. The scarfing roll 20 is generally in contact with and forms the upper surface 17 of the web 10, but may be positioned such that during a part of the cycle of the contouring roll there is no contact with the web 10. By way of example, the scarfing roll 20 may be positioned at a height of about $\frac{1}{4}$ inch from the upper side 13 of the belt 12, as measured from the largest diameter of the scarfing roll 20 to the upper side 13 of the belt 12, to form batts with an average basis weight in the range of from about 0.05 to about 0.08 gm/cm$^2$.

The scarfing roll 20 will generally be a high-speed rotating member, preferably rotating at a peripheral speed, or at a relative velocity between the web 10 and the scarfing surface 26, in the range of about 50 to about 60 fps, and most preferably about 55 fps. Under such conditions, it is presently preferred that the belt speed not exceed about 15 fps, and that the scarfing roll be rotated at a rate in the range of from about 5 to about 20 times per rotation of the contouring roll.

The teeth 22 of the scarfing roll 20 can be formed, for example, from a series of concentric metal discs defining pointed spokes and mounted upon a central shaft. It is contemplated that the discs at the center of the roll will generally define a smaller diameter than those at the marginal edges thereof, such that the basis weight of the scarfed batt will be greater at its central portions than at its marginal portions. Alternatively, the core of the roll 20 can itself be contoured, as shown in FIG. 1, and the teeth can be bristle-like members adhered thereto in a manner known in the art, such as by pressing into or through the core. It is presently preferred that the scarfing teeth 22 be distributed at an average density of at least about eight teeth per square inch, and no more than about 30 teeth per square inch. Typically, this tooth density would be about 12 teeth per square inch.

The contouring roll 30 should generally be cylindrically shaped, with one or more areas of smoothly increased radius, and positioned beneath the web 10, such that the web 10 is contoured by the contouring roll 30 in the direction of motion of the web 10. The contouring roll 30 may be positioned such that during a part of its rotation there is no contact with the web 10 or the belt 12. It is presently preferred that the contouring roll has a diameter in the range of from about 5 to about 10 inches.

The contouring roll 30 will generally rotate at the rate of one revolution per batt formed. Thus, when a knife 52 and anvil 54 arrangement is provided as shown by means of example in FIG. 2, a mechanical linkage 60 (such as gears, shafts and/or sprockets and chains or belts), synchronizes the rotation of the knife 52, the anvil 54 and the contouring roll 30. A typical phase adjusting mechanism normally would be included in the mechanical linkage. An example of such a mechanism is differential gearing, which can be purchased in packaged units from Fairchild Industrial Products Co. of Winston, Salem, N.C. Alternatively, it might be desired to rotate the contouring roll 30 a greater or lesser number of times per batt formed, depending on the specific application. For example, if very small batts are to be formed, it might be desirable to provide the contouring roll 30 with a nonuniform circumferential surface 32 having a repeating pattern of bowed surfaces 36 and flattened surfaces 38. Accordingly, a single revolution of the contouring roll 30 could be utilized to contour a plurality of batts 11. As yet another alternative, in some applications it might be desirable to form a repeating contour on a single batt, in which case the contouring roll could be operated to rotate at a rate of more than one revolution per batt formed.

It will be understood that many changes can be made to the details and parameters sets forth in the foregoing detailed description of the preferred embodiments, without departing from the intended spirit of the invention. Thus, it is the following claims, and all equivalents thereof, that are intended to define the scope of this invention.

I claim:

1. An apparatus for making a batt portion of a disposable absorbent structure from a continuously moving fibrous web
   having first and second opposing surfaces, said apparatus comprising:
   a movable belt for carrying the web;
   a toothed scarfing roll, rotatably mounted adjacent the first surface of the web and contoured along the length thereof in a direction transverse to the direction of movement of the fibrous web, for forming a transverse contour in the web by scarfing the first surface thereof;
   a contouring roll opposite said scarfing roll, said contouring roll having a nonuniform circumferential surface, disposed about a longitudinal axis thereof, in communication with the second opposing surface of the web and operatively synchronized with said scarfing roll for moving the second opposing surface relative to the axis of said scarfing roll during at least a partial revolution of said nonuniform circumferential surface and a full rotation of said scarfing roll to contour each batt formed thereby both transversely and longitudinally in the direction of movement of the web;
   and cutting means for cutting the fibrous web into a plurality of discrete batts at selected intervals.

2. The improvement of claim 1 wherein the scarfing roll is disposed above the web and the contouring roll is disposed below the web.

3. The improvement of claim 1 further comprising a knife and anvil arrangement, disposed downstream from the scarfing roll, operable to cut the fibrous web into a plurality of discrete batts at selected intervals.

4. The improvement of claim 3 wherein the contouring roll rotates no more than one revolution per scarfed batt.

5. The improvement of claim 4 wherein the contouring roll has a diameter in the range of from about 5 to about 10 inches, and rotates one revolution per batt formed.

6. The improvement of claim 1 wherein the scarfing roll rotates in the range of from about 5 to about 20 times per rotation of the contouring roll.

7. The improvement of claim 6 wherein the scarfing roll has a largest diameter in the range of from about 5 to about 7 inches and comprises a plurality of scarfing teeth distributed at an average density of about 8 to about 30 teeth per square inch.

* * * * *